United States Patent
Desmet (10) Patent No.: US 8,652,420 B2
(45) Date of Patent: Feb. 18, 2014

(54) DEVICE FOR THE DISTRIBUTION OF SAMPLE AND CARRIER LIQUID ACROSS A MICRO-FABRICATED SEPARATION CHANNEL

(75) Inventor: Gert Desmet, Elewijt (BE)

(73) Assignee: Vrije Universiteit Brussel, Brussels (BE)

( * ) Notice: Subject to any disclaimer, the term of this patent is extended or adjusted under 35 U.S.C. 154(b) by 592 days.

(21) Appl. No.: 12/601,237

(22) PCT Filed: May 23, 2008

(86) PCT No.: PCT/EP2008/056369
§ 371 (c)(1),
(2), (4) Date: Nov. 20, 2009

(87) PCT Pub. No.: WO2008/142160
PCT Pub. Date: Nov. 27, 2008

(65) Prior Publication Data
US 2010/0166611 A1    Jul. 1, 2010

(30) Foreign Application Priority Data
May 23, 2007 (WO) .................. PCT/EP2007/055008

(51) Int. Cl.
*B01L 3/00*    (2006.01)
(52) U.S. Cl.
USPC ............. 422/507; 422/70; 422/502; 422/503
(58) Field of Classification Search
USPC ............. 422/502, 503, 507, 70, 89; 436/161; 210/198.2, 656; 73/23.35–23.42, 73/61.52–61.58; 95/85; 96/107
See application file for complete search history.

(56) References Cited

U.S. PATENT DOCUMENTS

| | | | |
|---|---|---|---|
| 5,837,115 A * | 11/1998 | Austin et al. ................... | 204/450 |
| 6,156,273 A | 12/2000 | Regnier et al. | |
| 6,444,122 B1 * | 9/2002 | Van Davelaar ............ | 210/198.2 |
| 6,696,022 B1 * | 2/2004 | Chan et al. ..................... | 422/500 |
| 2005/0095602 A1 | 5/2005 | West et al. | |
| 2006/0065528 A1 | 3/2006 | Lopez et al. | |
| 2006/0285996 A1 | 12/2006 | Ohman et al. | |

FOREIGN PATENT DOCUMENTS

| | | |
|---|---|---|
| EP | 0 977 030 | 2/2000 |
| EP | 1 738 828 | 1/2007 |

OTHER PUBLICATIONS

Ajmera, et al. "Microfabricated Cross-flow Chemical Reactor for Catalyst Testing," *Sensors and Actuators B*, vol. 82, Nos. 2-3, pp. 297-306, Feb. 28, 2002.
De Pra, et al. "Experimental Study on Band Dispersion in Channels Structured with Micropillars,"*Analytical Chemistry*, vol. 78, No. 18, pp. 6519-6525, Sep. 15, 2006.

(Continued)

*Primary Examiner* — Jan Ludlow
(74) *Attorney, Agent, or Firm* — Knobbe, Martens, Olson & Bear LLP (57) ABSTRACT

The present invention relates to a chromatographic separation device comprising a first substrate body carrying a micro-fabricated separation channel recessed on one of its surfaces and covered by a second substrate body, both perforated with connection-holes for the supply and withdrawal of a sample and carrier liquid. The present device is characterized in that said micro-fabricated separation channel is preceded or succeeded by a flow distribution region that is filled with an array of micro-fabricated pillars, having a shape, size and positioning pattern selected such that said flow distribution region has a ratio of transversal to axial permeability of at least 2.

13 Claims, 7 Drawing Sheets

(56) References Cited

OTHER PUBLICATIONS

De Smet, et al. "Influence of the Pillar Shape on the Band Broadening and the Separation Impedance of Perfectly Ordered 2-D Porous Chromatographic Media," *Analytical Chemistry*, vol. 76, No. 13, pp. 3716-3726, Jul. 1, 2004.

Eghbali, et al. "Pressure-driven Chromatography in Perfectly Ordered Pillar Array Columns," LC-GC Europe (Online), pp. 1-11, dated Apr. 1, 2007, downloaded from www.lcgceurope.com.

International Search Report dated Oct. 8, 2008 and issued to a related international application.

* cited by examiner

DEVICE FOR THE DISTRIBUTION OF SAMPLE AND CARRIER LIQUID ACROSS A MICRO-FABRICATED SEPARATION CHANNEL

CROSS-REFERENCE TO RELATED APPLICATIONS

This application is the U.S. National Phase under 35 U.S.C. §371 of International Application PCT/EP2008/056369, filed May 23, 2008, which claims priority to PCT/EP2007/055008, filed May 23, 2007.

TECHNICAL FIELD

The present invention relates to the field of liquid chromatography. The invention provides a device and method for the distribution of sample and carrier liquid across a separation channel.

BACKGROUND

In the art of liquid chromatography, more and more devices are being developed that make use of microfabricated separation channels arranged on the surface of a polymer, silicon or glass wafer. Using etching techniques, said microfabricated separation channels usually have a flat-rectangular cross-section, i.e. are much wider than deep or are much deeper than wide.

To perform and detect a liquid chromatographic separation, said microfabricated separation channels are coupled to a sample injector and to a detector device. Traditionally, this coupling is ensured using a cylindrical connection capillary. The technological challenge surfacing here is that the liquid coming from a round tubing with limited diameter should be spread uniformly over the cross-section of said microfabricated separation channel without creating excessive band broadening or axial dispersion. Similarly, it is also important that at the end of the separation channel a distribution zone is arranged to make the transition between the flow in the flat-rectangular separation channel and the circular tubing needed to lead the sample towards an off-chip detector. If performing liquid chromatography, this transition should occur with a minimum of band broadening. One of the general engineering rules that can be used for the design of these flow distribution structures is that they should have a small total volume, for the band broadening or axial dispersion of a device is generally proportional to its volume.

With this in mind, a solution to disperse the liquid across a microchannel proposed in Sant et al. (2006, Reduction of End Effect-Induced Zone Broadening in Field-Flow Fractionation Channels, Anal. Chem., online publication A-H), and making use of a triangular distribution region with an opening angle between 60 and 90 degrees, has the clear drawback that it would occupy a too large volume if the ratio of separation channel width to inlet channel width is large. For example, if the separation channel would be 1 cm wide, the length of the distribution triangle in the case of 90 degree opening angle a would also have to be 1 cm. The continuously bifurcating channel inlet proposed in U.S. Pat. No. 6,156,273 also makes use of such a diverging channel inlet or outlet.

There is a need in the art for providing a device for the distribution of sample and carrier liquid across a micro-fabricated separation channel, which overcomes at least some of the above-indicated drawbacks.

SUMMARY

The present invention provides a device for the distribution of sample and carrier liquid in a micro-fabricated separation channel, wherein dispersion or permeability of the sample and carrier liquid across said separation channel is improved. In particular, the invention provides a device in which flow distribution zones are designed, wherein the lateral dispersion or permeability is promoted so as to become larger than the axial dispersion or permeability. Given that the incoming liquid needs to be spread in the lateral direction across the channel cross-section, such design is much more advantageous. It is noted that the flow distribution structures proposed in U.S. Pat. No. 6,156,273 and Sant et al. (2006) is that they have a lateral dispersion that is smaller than their axial dispersion.

Thereto, in all embodiments according to the present invention, a device is provided wherein flow distribution regions are developed that are filled, preferably over their entire depth, with an array of micro-fabricated pillars having a shape, size and positioning pattern selected such that said flow distribution region has a ratio of transversal to axial permeability of at least 2.

This permeability ratio can for example be calculated using computational fluid dynamics software to calculate the pressure drop of a flow progressing through the distribution region in the axial direction and comparing that with the pressure drop of a flow progressing through the distribution region in the transversal direction with the same mean velocity. The ratio of both pressure drops is then the inverse of the permeability ratio.

DETAILED DESCRIPTION OF THE INVENTION

The present invention relates to a flow distribution region designed to spread a liquid uniformly across the lateral width of a flat-rectangular separation channel containing a separation medium. Said separation medium can be another micro-pillar array, a bead packing, a monolithic support or any other suitable chromatographic medium.

The terms "distribution" and "dispersion" are used herein in some embodiments as synonyms and refer to the spatial property of being scattered about over an area or volume.

The term "permeability" as used herein refers to the rate of flow of a liquid through a material, preferably across a micro-fabricated separation channel as defined herein.

In a first embodiment the invention provides a chromatographic separation device comprising a first substrate body carrying a micro-fabricated separation channel recessed on one of its surfaces and covered by a second substrate body, both perforated with the necessary connection-holes for the supply and withdrawal of the sample and mobile phase liquid, characterized therein that said micro-fabricated separation channel is preceded or succeeded by a flow distribution region that is filled from bottom to top with an array of micro-fabricated pillars having a shape, size and positioning pattern selected such that said flow distribution region has a ratio of transversal to axial permeability of at least 2. Preferably, the invention relates to a chromatographic separation device comprising a first substrate body carrying a micro-fabricated separation channel recessed on one of its surfaces and covered by a second substrate body, whereby said first and said second substrate body are both perforated with inlet and outlet connection-holes for the supply and withdrawal of a sample and carrier liquid, characterized in that said micro-fabricated separation channel is preceded or succeeded by a flow distribution region that is filled with an array of micro-fabricated pillars, whereby said pillars have a shape, size and positioning pattern selected such that said flow distribution region has a ratio of transversal to axial permeability of at least 2.

In a preferred embodiment, said flow distribution region has a substantially uniform lateral width, said width being equal to the width of said separation channel.

In another embodiment, a device is provided wherein said micro-fabricated pillars have a diamond-like or ellipsoidal shape. Preferably said micro-fabricated pillars have a ratio of lateral width to axial width that is larger than 3/2.

In a preferred embodiment, the invention relates to a device wherein said micro-fabricated pillars are arranged in different zones of different pillar sizes, whereby said different zones are arranged in a substantially monotonic order from the zone containing the smallest pillars to the zone containing the largest pillars, and whereby the zone containing the largest pillars is arranged closest to the inlet or outlet connection hole of said substrate body.

Even more preferred, a device is provided wherein said micro-fabricated pillar zone having the largest pillars is adjacent to an open zone devoid of pillars. Said open zone preferably has a width of 1 to 20 μm.

Figure 1A:
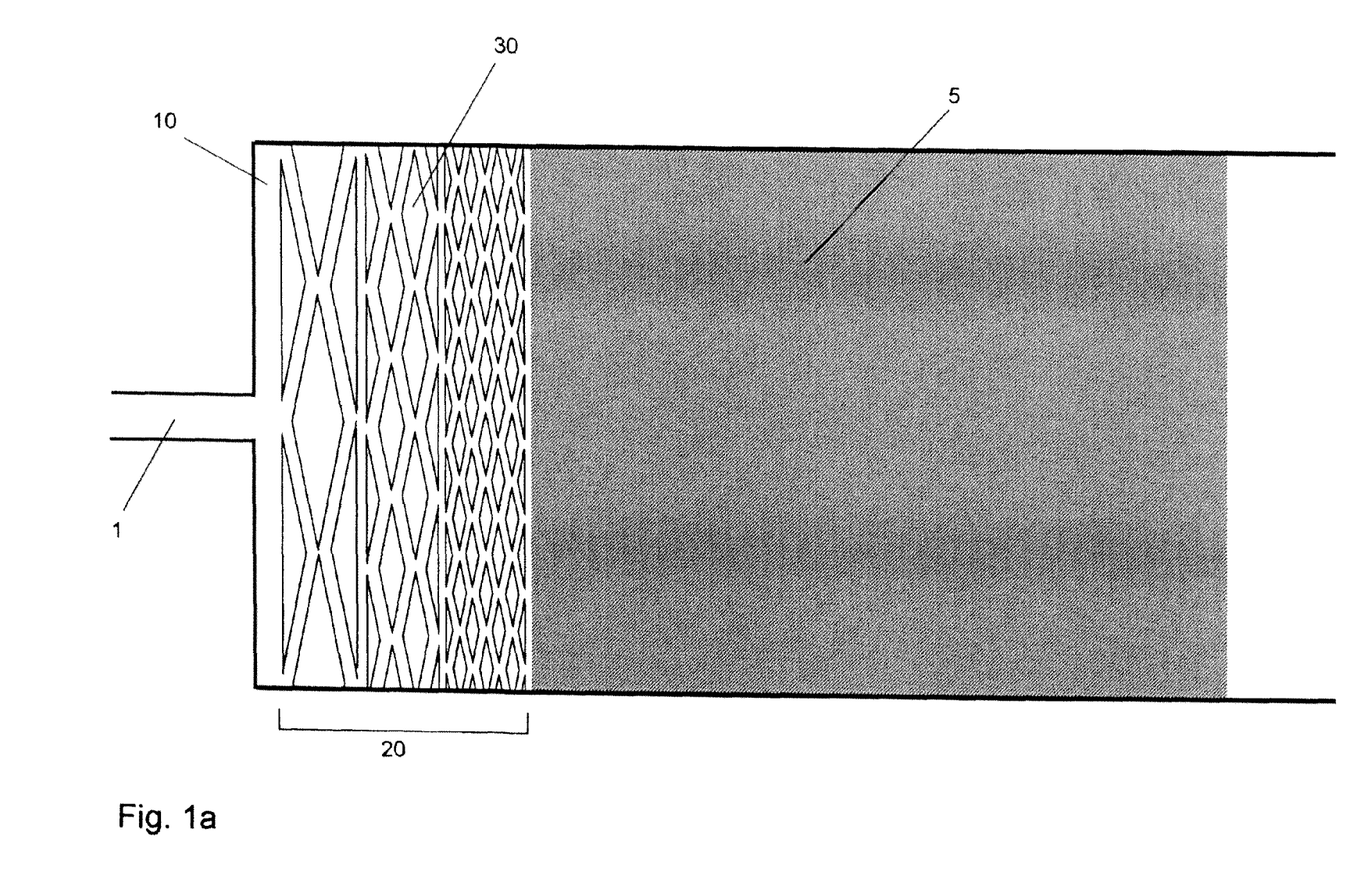
FIG. 1a is a top view of a separation channel being arranged with one of the flow distribution regions according the present invention.

FIG. 1a shows an embodiment of a flow distribution region according the present invention and preceding a separation channel filled with a separation medium 5, comprising a short open region 10, constituting a flow domain wherein the resistance against the flow in the lateral direction is minimal, preferably 1 to 10 μm wide and being directly connected to the inlet orifice 1, followed by a flow distribution region 20 according to the present invention comprising micro-machined pillars 30 having a ratio of lateral width 31 to axial width 32 (FIG. 1b) that is larger than 3/2 and sufficiently closely packed to induce a lateral permeability that is at least 2 times larger than the axial permeability. In a preferred embodiment, said micro-machined pillars are arranged in order of decreasing size, with the largest pillars closest to the inlet orifice 1 of the substrate body carrying said separation channel. At the channel outlet, the different regions making up the flow distribution regions should be arranged in an opposite order, starting with the smallest flow distribution pillars and ending with the open region.

Figure 1B:
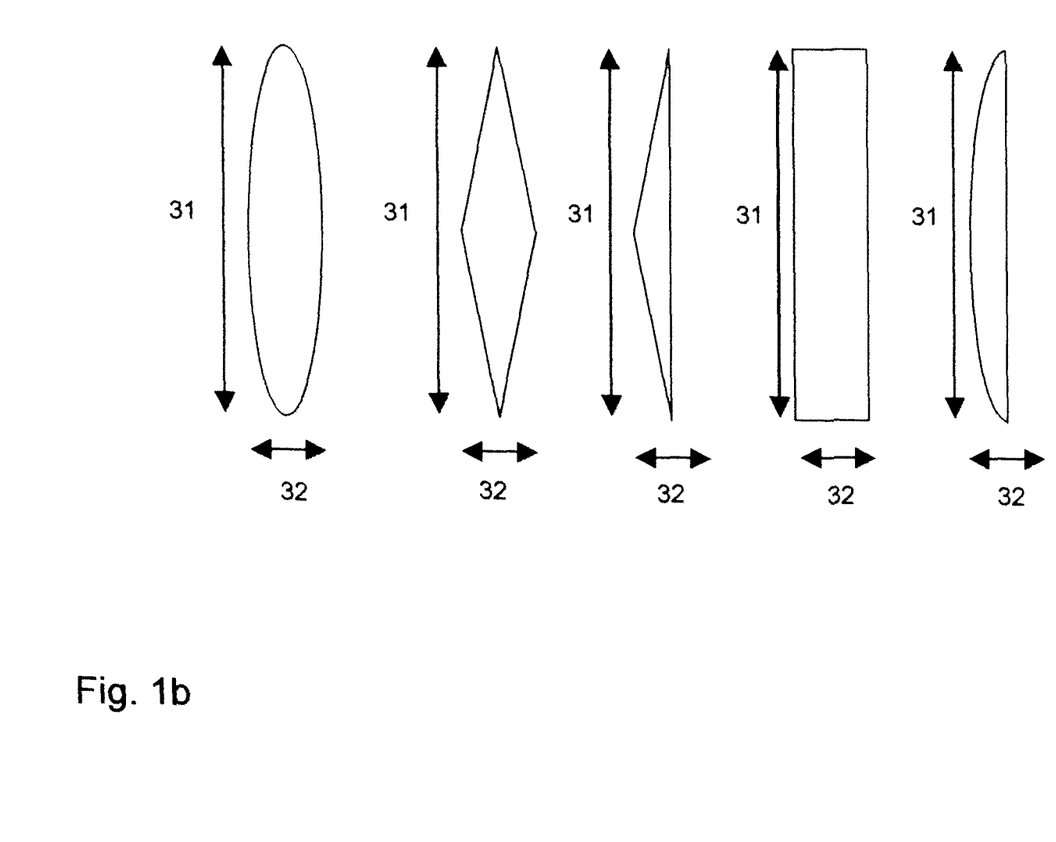
FIG. 1b illustrates examples of micro-pillar shapes with a suitable lateral width to axial width ratio.

FIG. 1b shows a top view of a number of the possible micro-fabricated pillar shapes that can be effective for use in the flow distribution region(s) according to the present invention. The terms "micro-fabricated" or micro-machined are used herein as synonym. Methods to produce the desired micro-pillars are well-known to those skilled in the art of micromachining, and are for example Bosch etching or LIGA replication. Substrates suitable to produce the micro-pillars are for example glass wafers or silica wafer. The terms "micro-pillar" or "pillar" as used herein refer to structures that have been fabricated using a micromachining technique.

Figure 2:
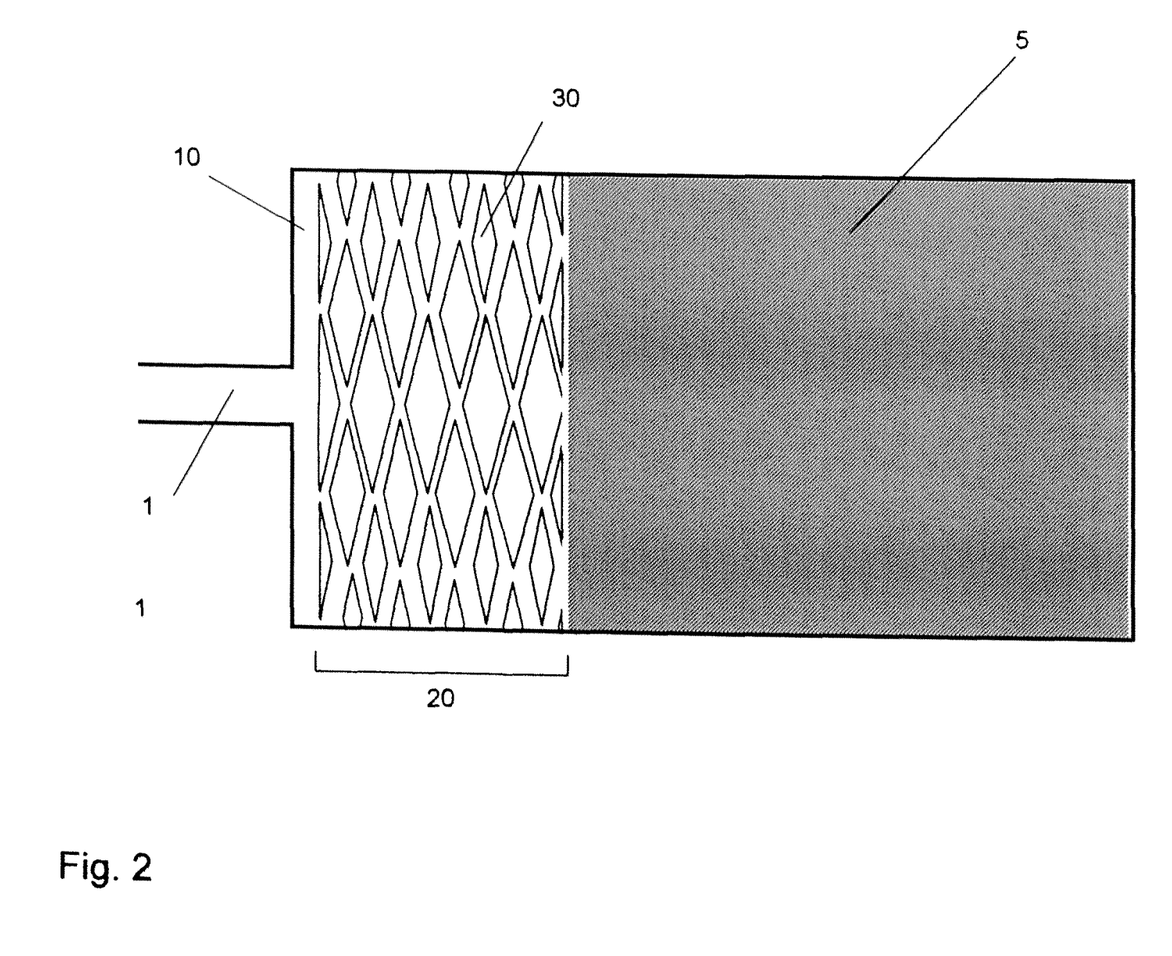
FIG. 2 is a top view of one of the flow distribution regions according the present invention, consisting of pillars with a size and/or inter-pillar distance that varies in the lateral direction.

In another embodiment, the invention provides a device wherein the size and the inter-pillar distance of said micro-pillars is varied in lateral direction. To promote a further good lateral distribution of the liquid, it also one of the aspects of the present invention to provide a pattern of pillars with a size and/or inter-pillar distance that varies in the lateral direction so as to have a flow distribution region having a lower flow resistance in the lateral channel parts that are most remote of the inlet and/or outlet orifices. Such embodiment is for instance illustrated on FIG. 2.

Figure 3:
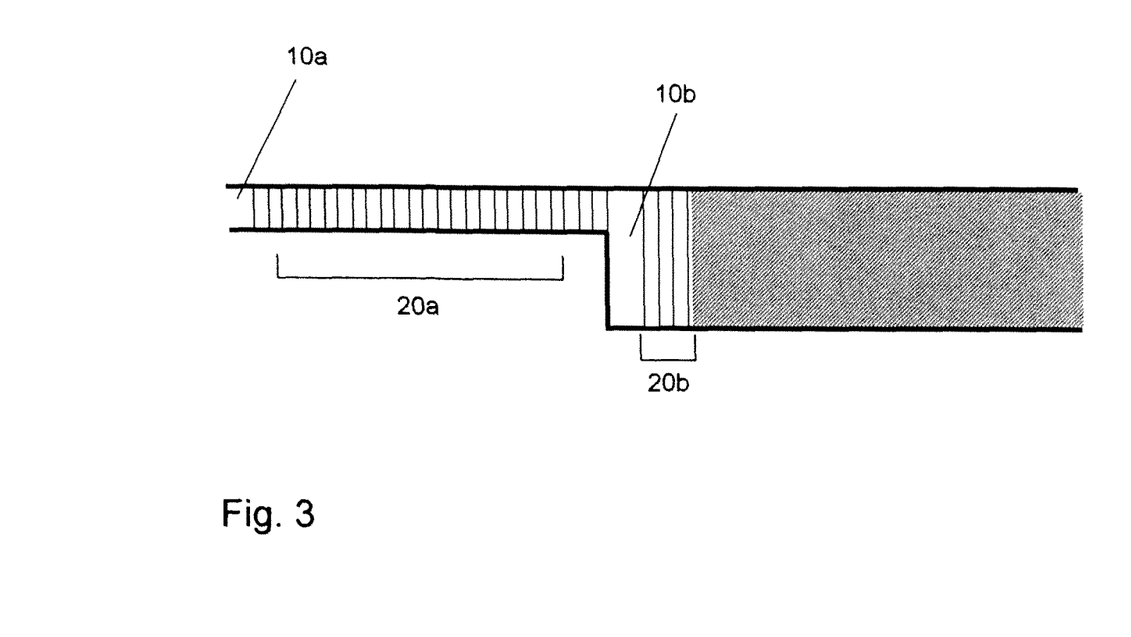
FIG. 3 is a longitudinal cross-sectional view of one of the flow distribution regions according the present invention, wherein at least one part of the flow distribution region is etched to a lesser depth than said separation channel.

In yet another preferred embodiment, at least one part of the flow distribution region has a lesser depth than said separation channel, i.e. it is etched to a lesser depth than said separation channel. FIG. 3 shows such an embodiment, wherein the open region 10a and a first part of the flow distribution region 20a is etched to a significantly lesser depth than the separation channel containing the separation medium 5 and the second part of the flow distribution region 20b, preferably also preceded by an open region 10b. The advantage of this embodiment is that a further reduction of the volume of the flow distribution region is created. In some embodiments according to the present invention, said deeper etched second part 20b can be omitted. In some case however, a particular advantage of deeper etched second part 20b of said flow distribution can be obtained by selecting the pillar sizes and inter-pillar dimensions such that the axial permeability of said second part is very low. This will help to induce a convective flow in the open region 10b that runs essentially in the downward direction, hence promoting the mixing across the depth of the separation channel.

Figure 4:
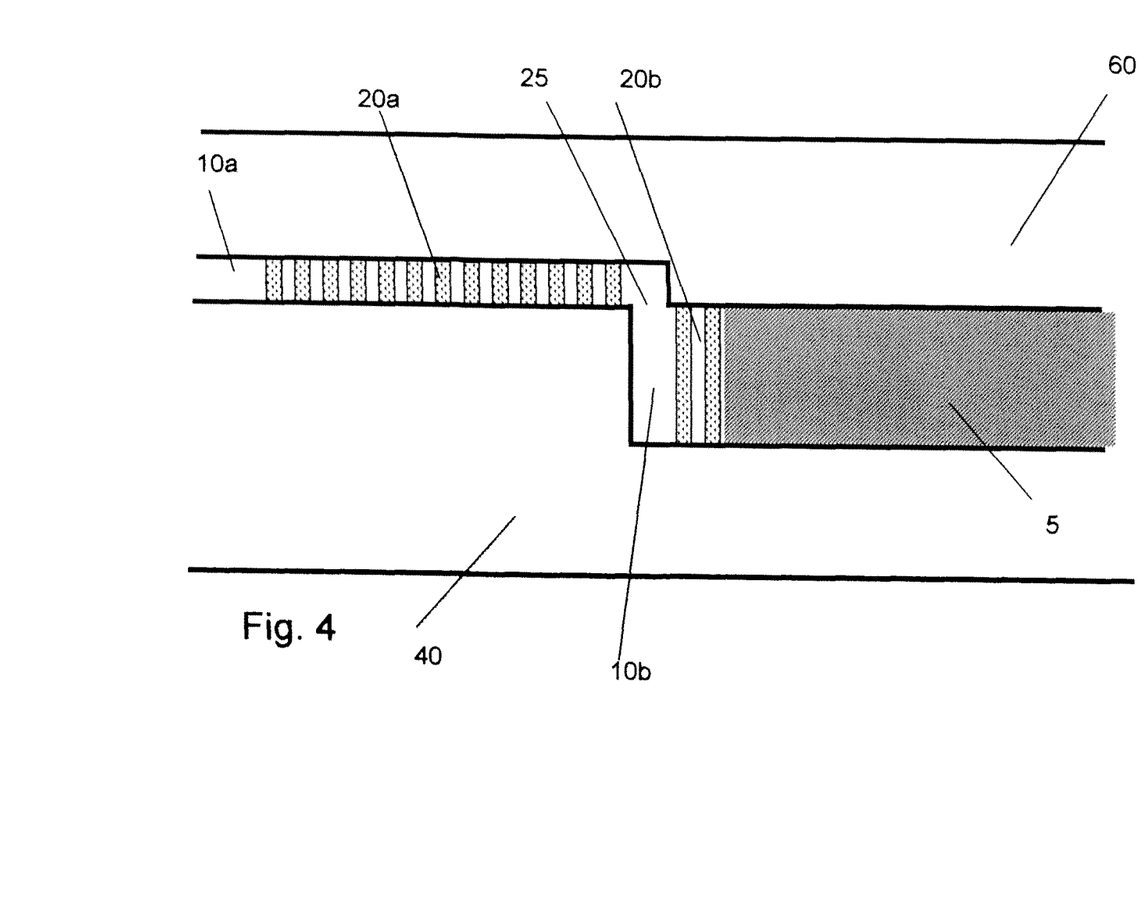
FIG. 4 is a longitudinal cross-sectional view of a device according to the present invention wherein a flow distribution region is arranged on a surface different from the surface carrying the separation channel.

In another embodiment, the invention provides a device, wherein at least one part of the flow distribution region is arranged on a different surface than the surface carrying said separation channel. The present invention is not limited to flow distribution regions that are arranged on the same surface as the surface carrying said separation channel. As represented in FIG. 4, the use of a perpendicularly etched connection channel 25 allows at least a part of the flow distribution region 20a to be arranged on either the surface of the substrate body 40 carrying the separation channel filled with the separation medium 5 (opposite to the surface carrying the separation channel), or on one of the surfaces of the substrate body 60 used to close off the separation channel. The advantage of these embodiments is that the perpendicular running connection channel 25 will induce a perpendicular flow to the separation channel, hence promoting mixing in the depth of the channel.

Figure 5:
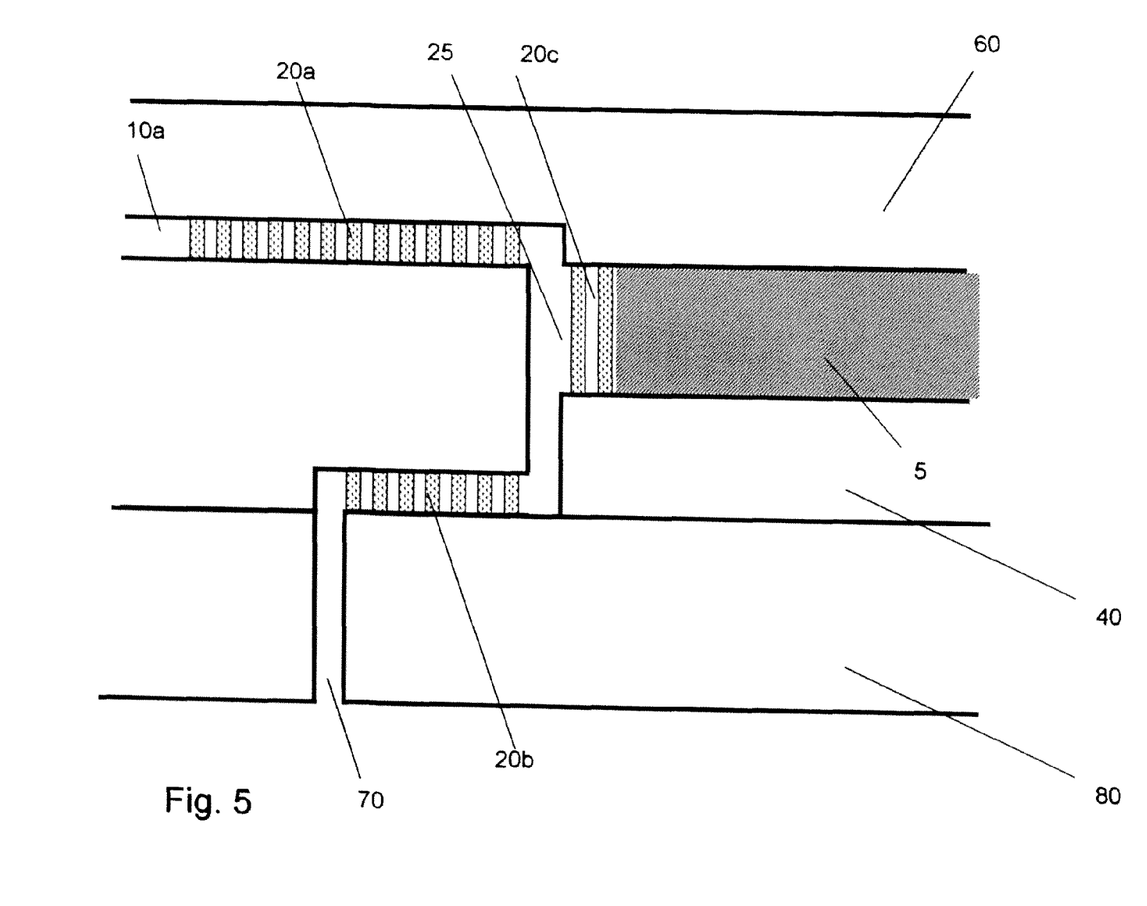
FIG. 5 is a longitudinal cross-sectional view of a device according to the present invention wherein two different flow distribution regions are connected to different inlet reservoirs.

In another embodiment according to the present invention, a device may be provided wherein at least two different flow distribution regions are present at a different surface and are connected to a different liquid reservoir. Multiple inlet flows coming from different fluid reservoirs can be used. For example, as represented on FIG. 5, one inlet flow is provided that feeds a first distribution region 20a, and a second inlet flow is provided that feeds a second distribution region 20b, and that enters the separation device via a second inlet orifice 70 machined in a third substrate 80 used to close off the second distribution region 20b (FIG. 5). The advantage of this embodiment is that the sample to be separated can be sent through a flow distribution region that is smaller—hence creating less band broadening—than the flow distribution region used for the main mobile phase flow or carrier fluid. Both separate inlet flows can be organized alternately or simultaneously.

Figure 6A:
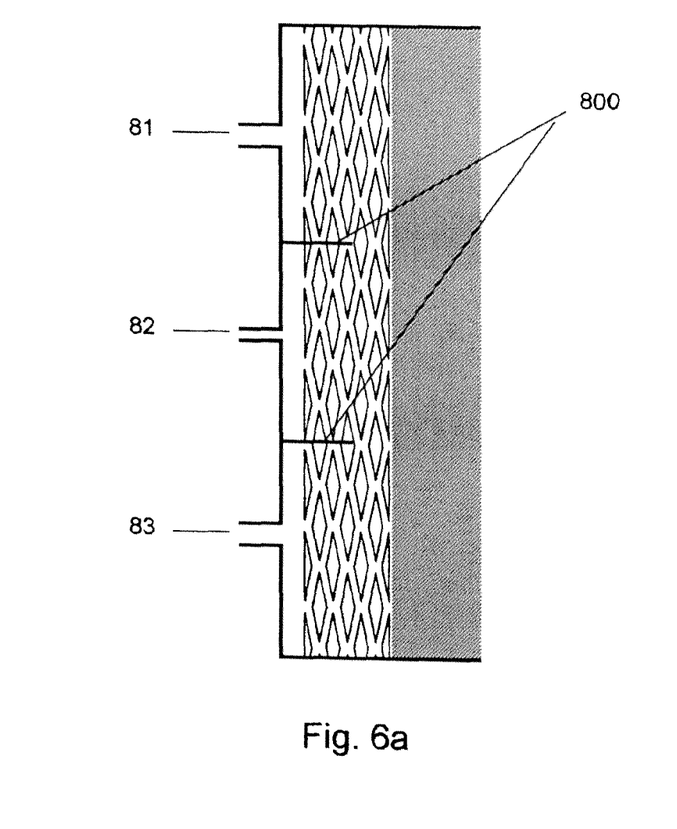
FIG. 6a-b illustrate a top view of one of the flow distribution regions according the present invention having parallel running separation walls and connected to different (FIG. 6a) inlet or (FIG. 6b) outlet channels.
Figure 6B:
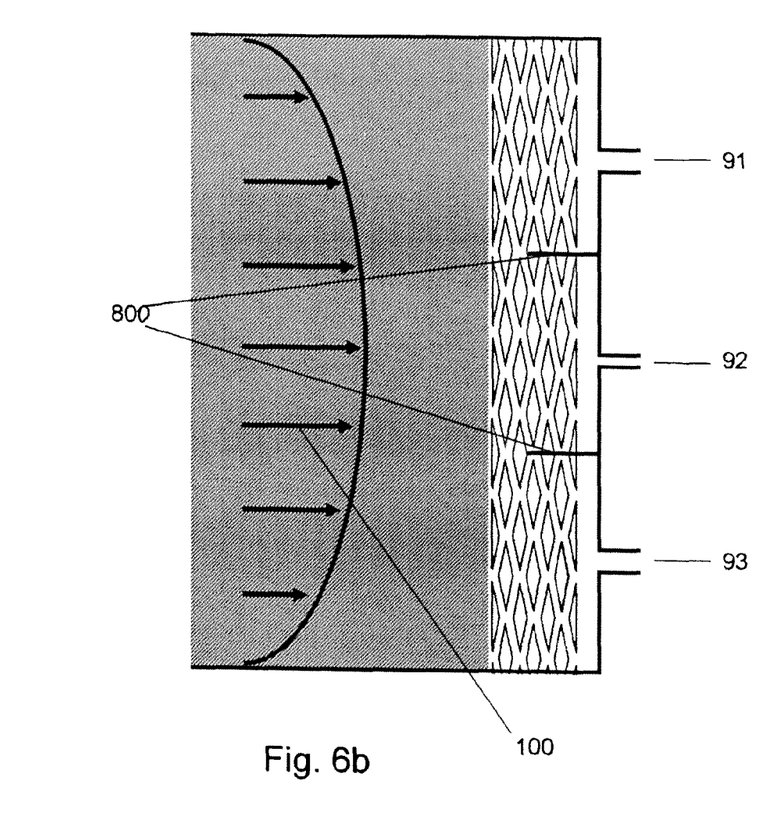

In yet another embodiment according to the present invention, a device is provided, wherein said flow distribution region is provided with one or more impermeable thin walls, which at least partly divide said flow distribution regions in two or more sections, said walls being provided parallel with the mean flow direction, and wherein preferably said sections are each connected to a different in- or outlet channel. For instance, the flow distribution region is at least partly divided using n impermeable thin walls 800, n being larger than 1, running parallel with the mean flow direction and hence preventing the communication between different lateral parts of the flow distribution region. FIG. 6a illustrates how this approach can be used to feed the sample to the central part of the channel only, using separate feeding channels 81, 82 and 83. FIG. 6b illustrates how this approach can be used to feed the liquid running through the central part of the channel exclusively to the detector device using a first outlet channel 91, while the liquid flowing closest to the channel side walls is evacuated to the waste using a second and a third outlet channel 92 and 93. Arranging said flow dividing impermeable walls into the flow distributor region is especially advantageous because the flow distributor will anyhow also limit the band broadening induced by the transition between the broad separation channel and the narrow in- and outlet channels and also because the high flow resistance of the distributor regions according to the present invention allows alleviating the influence of differences in flow resistance among the parallel inlet channels or among the parallel outlet channels by making the flow resistance of said parallel inlet and outlet channels negligible compared to the flow resistance of the flow distributor region.

Limiting the injection and detection of species to the central region of the channel can be expected to be very advantageous if the flow distributing device itself functions improperly and leads to a warped velocity profile 100. In this case it would be advantageous to only inject and/or detect in the central part of the channel, where the warp of the velocity profile will anyhow be much smaller than near the side-walls. It will also be very advantageous to circumvent the side-wall dispersion problem described in Broeckhoven and Desmet (Journal of Chromatography A, 1172 (2007), 25-39).

The present invention further relates to a method for controlling dispersion and/or permeability of a sample and carrier liquid across a micro-fabricated separation channel having inlet and outlet connection-holes for respectively the supply and the withdrawal of said sample and carrier liquid, said method comprising inducing a lateral permeability that is larger than an axial permeability. Preferably, said method comprises inducing a lateral permeability that is at least 2 times larger than said axial permeability. The present method is carried out by providing in the front of, or in the back of said micro-fabricated separation channel a flow distribution region that is filled with an array of micro-fabricated pillars. Said pillars have a shape, size and positioning pattern as defined herein and selected such that said flow distribution region provides a ratio of transversal to axial permeability of at least 2.

In another embodiment, the invention provides a method for controlling flow dispersion or permeability of a sample and carrier liquid across a micro-fabricated separation channel comprising inducing in the lateral parts of said separation channel that are most remote of said connection holes a lower flow resistance. This embodiment can be obtained by adapting shape, size, positioning pattern, and/or inter-pillar distance of said micro-pillars in the lateral direction of said micro-fabricated separation channel.

The invention further provides a method comprising separately controlling the permeability (dispersion) of said sample and said carrier liquid.

What is claimed is:

1. A chromatographic separation device comprising, directly extending into each other in the fluid flow direction:
   a) an inlet channel;
   b) optionally, an open region of 1-20 μm;
   c) a first flow distribution region that is filled with an array of micro-fabricated pillars, the width of said first flow distribution region being more than doubled with respect to the width of said inlet channel and whereby
      said pillars have a diamond-like or ellipsoidal shape with a ratio of lateral width to axial width that is larger than 3/2,
      said pillars are in a diagonal alternating arrangement forming laterally extending interconnected channels, and
      the size and the positioning of said pillars is such that said first flow distribution region has a ratio of transversal to axial permeability of at least 2;
   d) a micro-fabricated separation channel;
   e) a second flow distribution region that is filled with an array of micro-fabricated pillars, whereby
      said pillars have a diamond-like or ellipsoidal shape with a ratio of lateral width to axial width that is larger than 3/2,
      said pillars are in a diagonal alternating arrangement forming laterally extending interconnected channels, and
      the size and the positioning of said pillars is such that said second flow distribution region has a ratio of transversal to axial permeability of at least 2;
   and
   e) an outlet channel; the width of said second flow distribution region being more than doubled with respect to the width of said outlet channel;
   wherein said micro-fabricated separation channel comprises a micro-pillar array with micro-pillars substantially smaller in diameter than the micro-fabricated pillars of said first and said second flow distribution region.

2. The chromatographic separation device according to claim 1, wherein within said first flow distribution region said micro-fabricated pillars are arranged in different zones of different pillar sizes, whereby said different zones are arranged in a substantially monotonic order from a zone containing the smallest pillars to a zone containing the largest pillars, and whereby said zone containing the largest pillars is arranged closest to said inlet channel.

3. The chromatographic separation device according to claim 1, wherein within said second flow distribution region said micro-fabricated pillars are arranged in different zones of different pillar sizes, whereby said different zones are arranged in a substantially monotonic order from a zone containing the smallest pillars to a zone containing the largest pillars, and whereby said zone containing the largest pillars is arranged closest to said outlet channel.

4. The chromatographic separation device according to claim 1, wherein said micro-fabricated separation channel is formed by a first substrate body having micro-fabricated channels recessed on one of its surfaces, which channels are covered by a second substrate body.

5. The chromatographic separation device according to claim 1, wherein the size and the inter-pillar distance of said micro-fabricated pillars in said first and/or second flow distribution region is varied in lateral direction.

6. The chromatographic separation device according to claim 1, wherein at least one part of said first and/or second flow distribution region has a lesser depth than said micro-fabricated separation channel.

7. The chromatographic separation device according to claim 1, wherein said micro-fabricated separation channel and said first and/or second flow distribution regions are each formed on a surface, and at least one part of the first and/or second flow distribution region is arranged on a surface which is different from the surface on which said micro-fabricated separation channel is formed.

8. The chromatographic separation device according to claim 1, comprising two or more first flow distribution regions wherein said first flow distribution regions are connected to different liquid reservoirs through a different inlet channel.

9. The chromatographic separation device according to claim 1, wherein one or both of said first and second flow distribution region is/are provided with one or more impermeable thin walls, which at least partly divide said flow distribution region in two or more sections, said walls being provided parallel with the mean flow direction, and wherein each of said sections is connected to a different inlet and/or outlet channel.

10. The chromatographic separation device according to claim 1, wherein said device further comprises a sample injector connected to said inlet channel through a cylindrical connection capillary.

11. The chromatographic separation device according to claim 1, wherein said device further comprises a detector device connected to said outlet channel through a cylindrical connection capillary.

12. The chromatographic separation device according to claim 1, wherein said device comprises an open region devoid of micro-fabricated pillars between said inlet channel and said first flow distribution region, the width of said open region being 1-10 μm.

13. A method for the chromatographic separation of a sample by a micro-fabricated separation channel, said method comprising introducing the sample into a chromatographic device according to claim 1, thereby improving the dispersion and/or permeability of said sample and carrier liquid across said micro-fabricated separation channel.

* * * * *